(12) United States Patent
Stagliano et al.

(10) Patent No.: US 6,828,347 B2
(45) Date of Patent: Dec. 7, 2004

(54) ANTI-VIRAL MULTI-QUINONE COMPOUNDS AND REGIOSPECIFIC SYNTHESIS THEREOF

(75) Inventors: Kenneth William Stagliano, Chicago, IL (US); Ashkan Emadi, Chicago, IL (US)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 10/288,685

(22) Filed: Nov. 6, 2002

(65) Prior Publication Data

US 2004/0087663 A1 May 6, 2004

(51) Int. Cl.[7] .................... C07D 307/77; A61K 31/122; A61K 31/35; C07C 50/04

(52) U.S. Cl. ........................ 514/454; 514/685; 549/293; 549/296; 549/297; 552/389; 552/390; 552/391

(58) Field of Search ................................ 549/297, 296, 549/293; 552/389, 390, 391; 514/454, 685

(56) References Cited

U.S. PATENT DOCUMENTS

| | | | |
|---|---|---|---|
| 4,032,548 A | 6/1977 | Martin et al. | 552/390 |
| 4,038,293 A | 7/1977 | Smith et al. | 552/389 |
| 4,460,678 A | 7/1984 | Yu et al. | 549/296 |
| 4,532,078 A | 7/1985 | Yu et al. | 559/297 |
| 4,592,867 A | 6/1986 | Yu et al. | 552/296 |
| 4,632,782 A | 12/1986 | Komatsu et al. | 552/296 |
| 4,698,184 A | 10/1987 | Yu et al. | 557/297 |
| 4,786,652 A | 11/1988 | Venuti | 514/481 |
| 4,880,571 A | 11/1989 | Comninellis et al. | 514/325 |
| 5,608,092 A | 3/1997 | Hamamura et al. | 552/225 |
| 5,639,718 A | 6/1997 | Patil | 514/297 |
| 5,672,607 A | 9/1997 | Boyd et al. | 552/389 |
| 5,679,808 A | 10/1997 | Mizoguchi et al. | 514/454 |
| 5,744,623 A | 4/1998 | Garcia Gravalos et al. | 514/456 |
| 5,783,598 A | 7/1998 | Boyd et al. | 552/389 |
| 5,869,522 A | 2/1999 | Boyd et al. | 514/454 |
| 5,977,389 A | 11/1999 | Okada et al. | 552/390 |
| 6,022,658 A | 2/2000 | Hamasaki | 430/55 |
| 6,103,700 A | 8/2000 | Bandiera et al. | 514/39 |
| 6,162,799 A | 12/2000 | Khambay et al. | 514/63 |

FOREIGN PATENT DOCUMENTS

JP 59-212444 1/1984

OTHER PUBLICATIONS

Yin et al , J. Org. Chem. Comm. (1998) vol. 63 pp 5726–5727.*
Laatsch, Liebigs Annalen der Chemie (1983), (11), 1886–1900 Chem Abs.*
Patai, The Chemistry of the Quinonoid Compounds Part 2, (1974), pp 812–813.*

Laurent A. Decosterd et al.: *Structure, Absolute Sterochemistry, and Synthesis of Conocurvone, a Potent, Novel HIV–Inhibitory Naphthoquinone Trimer from a Conospermum sp., J. Am. Chem. Soc.* pp. 6673–6679, vol. 115, 1993.

James A. Armstrong et al.: *Constituents of Conospermum brachyphyllum. Improved methods for the Isolation and Synthesis of (+) –Conocurvone and the Structure of (+) – Brachyphyllone, Aust. J. Chem*, pp. 57–62, vol. 52, 1999.

Hartmut Laatsch: *Conocurvone–Prototype of a New Class of Anti–HIV Active Compound?. Angew. Chem. Int. Ed. Engl.*, pp. 422–425, vol. 33, No. 4, 1994.

M. Kearney et al.: *Understanding Antiviral Drug Resistance, First HIV DRP Symposium*, Dec. 2000.

Karen Grierson: *Antiviral Research–13th International Conference (Part VII)*, www.current–drugs.com, pp. 1–5, Apr. 2000.

Jin–Rui Dai et al.: *Novel Naphthoquinones From Conospermum Incurvum, Journal of Natural Products*, pp. 1511–1516, vol. 57, No. 11, Nov. 1994.

Susan L. Vander Velde et al.: *Kinetic Resolution of Racemic Chromenes via Asymmetric Epoxidaton: Synthesis of (+) —Teretifolione B. J. Org. Chem.*, 5380–5381, vol. 60, No. 17, 1995.

J. R. Cannon et al.: *Structures of Nine Quinones Isolated From Two Conospermum Species, Tetrahedron Letters*, No. 32, pp. 2795–2798, 1975.

Ashkan Emadi et al.: *Regiocontrolled Synthesis of the Trimeric Quinone Framework of Conocurvone, Organic Letters*, pp. 521–524, vol. 4, No. 4, 2002.

Rudolf Pummerer et al.:*Zur Kenntnis der Polymerisationsvorgänge, Die Kondensation von Naphthochinon–(1.4) zu Triphthaloylbenzol durch Pyridin.* pp. 2569–2583, No. 12, 1938.

(List continued on next page.)

*Primary Examiner*—Cecilia J. Tsang
*Assistant Examiner*—Raymond Covington
(74) *Attorney, Agent, or Firm*—Pauley Petersen & Erickson

(57) ABSTRACT

This invention provides various biquinone and trimeric quinone derivatives. The invention also provides a method for synthesis of a multi-quinone compound including reacting a hydroxyquinone anion with a first quinone possessing a first directing group at a C-2 of the first quinone and a second directing group at a C-3 of the first quinone and obtaining a biquinone having one of the first and second directing groups at a C-3 of a first quinone monomer and a hydroxyl group at a C-3' of a second quinone monomer. The biquinone can be further reacted to obtain various biquinone derivatives or with a second hydroxyquinone anion to obtain trimeric quinone derivatives, including trimeric naphthoquinone derivatives. The biquinones and trimeric quinones of this invention demonstrate antiviral activity and can be used to treat viral infections, particularly HIV infections.

21 Claims, No Drawings

OTHER PUBLICATIONS

Kenneth W. Stagliano et al.: *Regiospecific Synthesis of Unsymmetrical 2,3–Diarylquinones via Stepwise Pd(0)–Catalyzed Couplings of Arylstannanes to Doubly Activated Quinone Equivalents*, Tetrahedron Letters, pp. 6617–6620, vol. 38, No. 38, 1997.

Kenneth W. Stagliano et al.: *Regioselective Directed ortho Metalation, of 3H–Naphtho [2,1–b]pyrans. Synthesis of Methylteretifolione B*. Tetrahedron Letters, Vol. 39, pp. 4941–4942, 1998.

Kenneth W. Stagliano et al.: *Regiospecific Synthesis of 2,3–Bisnaphthopyranyl Quinones Related to Conocurvone. Effect of Substituents on Palladium–Catalyzed of Cross–Coupling of Organostannanes to Naphthopyranyl Hydroxyquinone Trflates*, J. Org. Chem., pp. 8034–8040, vol. 64, No. 21, 1999.

Jingjun Yin et al.: *A synthesis of Trisquinones*, J. Org. Chem. pp. 5726–5727, vol. 63, No. 17, 1998.

Hartmut Laatsch: *Studies in the Synthesis of Helical Naphthoquinone Oligomers, 1. 2.2';3'.2"–Ter– and 2.2';3'.":3".2'"–Quarter (1.4–naphthoquinone)*, Liebigs Ann. Chem. pp. 433–440, 1990.

X. Jiang et al.: *First examples of reactions of carbene complexes with conjugated triynes: a novel synthesis of trimeric quinones*, New Reactions and Methodology Symposium (Abstract), American Chemical Society 2001, ORGN–681.

Rudi Pauwels et al.: *Rapid and Automated Tetrazolium–based Colorimetric Assay for the Detection of Anti–HIV Compounds*, Journal of Virological Methods, vol. 20, pp. 309–321, 1988.

Ashkan Emadi and Kenneth W. Stagliano: *Regiospecific Synthesis of 3–Aryl–2, 2'–Biquinones*, National Meeting of the American Chemical Society, Chicago, IL, *Powerpoint Presentation*, Aug. 2001.

\* cited by examiner

US 6,828,347 B2

ANTI-VIRAL MULTI-QUINONE COMPOUNDS AND REGIOSPECIFIC SYNTHESIS THEREOF

GOVERNMENT INTEREST

This invention was made with government support under NIH Grant #AI43687 awarded by the National Institutes of Health. The U.S. Government has certain rights in the invention as provided in the grant.

FIELD OF INVENTION

The present invention relates to a method of regiospecific synthesis of multi-quinone compounds. The invention also relates to novel biquinones and trimeric quinones, particularly those that have antiviral activity.

BACKGROUND OF THE INVENTION

Acquired immune deficiency syndrome (AIDS) is a fatal disease caused by the human immunodeficiency virus (HIV) that afflicts millions of people worldwide. Many current commercially available drugs used to treat HIV act by inhibiting either the enzymes reverse transcriptase or protease. The use of combinations or cocktails of these two classes of drugs has enabled a great number of HIV-infected individuals to keep the virus in check and stay alive. Some patients, however, do not respond to multi-drug therapy, and side effects of several current drugs can be serious. In many cases, HIV develops resistance to existing therapies, and thus there is an urgent need for the continued development of new classes of anti-HIV agents. The seriousness of the AIDS epidemic has resulted in an effort to discover novel HIV inhibitory agents from natural sources as well as man-made drugs.

U.S. Pat. Nos. 5,672,607; 5,783,598; and 5,869,522, all issued to Boyd et al., disclose the isolation of conocurvone from a plant of the genus Conospermum, commonly known as the western Australian smoke bush. The chemical structure of conocurvone was determined to be a trimeric naphthoquinone derivative. The Boyd et al. Patents disclose that conocurvone had been found to inhibit the growth and replication of viruses, and particularly retroviruses such as an HIV.

The Boyd et al. Patents disclose methods of isolating and purifying naturally occurring trimeric naphthoquinone derivatives from plants of the genus Conospermum. In addition, the Boyd et al. Patents disclose synthesizing trimeric naphthoquinones through acid-coupling or base-coupling a 2,3-deoxy-1,4-napthoquinone compound with two other naphthoquinone monomers. The result of this process is a mixture of numerous monomeric naphthoquinone, dimeric naphthoquinone, and trimeric naphthoquinone derivatives. The trimeric naphthoquinone is isolated, purified, and identified by the anti-HIV properties through immunoassay. The Boyd et al. Patents disclose that the naphthoquinone derivatives can be easily distinguished from the monomeric and dimeric naphthoquinones as these compounds were both found to be devoid of antiviral activity. The observed biological activity of conocurvone was thus attributed to the trimeric quinone structure.

Conocurvone and other trimeric quinones may possess a completely novel mechanism of HIV-inhibition by acting against integrase and fusion of HIV to CD4 T-lymphocytes. Therefore, there is a need for methods for synthesis of chemical compounds having a trimeric quinone structure. There is also a need for methods of trimeric quinone synthesis that allow more control over the specific quinone derivatives formed, and provides increased yields of the desired quinone derivatives.

There is a need for a method that can be used to controllably produce various multi-quinone derivatives to facilitate structure-activity-relationship studies that will be crucial to the possible development of new anti-HIV quinone compounds and medicinal compositions. Thus there is a need for dimeric quinone derivatives, and methods to form the dimeric quinone derivatives, which can be used to controllably synthesize trimeric quinone derivatives.

SUMMARY OF THE INVENTION

A general object of the invention is to provide a method for regiospecific synthesis of multi-quinone compounds. A more specific objective of the invention is to overcome one or more of the problems described above. The general object of the invention can be attained, at least in part, through a method for synthesis of a multi-quinone compound including reacting a hydroxyquinone anion with a first quinone possessing a first directing group at a C-2 of the first quinone and a second directing group at a C-3 of the first quinone and obtaining a biquinone having one of the first and second directing groups at a C-3 of a first quinone monomer and a hydroxyl group at a C-3' of a second quinone monomer. One of the first and second directing groups is selected from a group consisting of fluorine, chlorine, bromine, iodine, and a non-halogen, and another of the first and second directing groups is selected from a group consisting of iodine and a non-halogen.

The biquinone can be further reacted in the presence of a base to substitute the hydroxyl group with a different chemical group, such as an alkyl ether, a halogen, an amine, a sulfonate ester, an aryl, a heteroaryl, an aryl ester, an alkyl ester, an alkyl amide, an aryl amide, or a carbamate. The biquinone can also be further reacted with a nucleophile. The nucleophile can substitute for the other of the first and second directing group. The nucleophile, for example, can be an amine analog or a second hydroxyquinone anion. Reacting the biquinone with the second hydroxyquinone anion results in a trimeric quinone. The invention also relates to various biquinone derivatives and trimeric quinone derivatives.

The invention relates to a method for treating a viral infection by administering to a host an antiviral biquinone compound including a first group at a C-3 position and a second group at a C-3' position. The first group can include a halogen, an ester group, an amide group, a carbamate group, an alkoxyl group, a hydroxyl group, a thiol group, a sulfide group, a primary aliphatic amine, a secondary aliphatic amine, a tertiary aliphatic amine, a cyclic amine, an alkyl, a functionalized alkyl, an alkyne, an alkene, an aryl, or a heteroaryl. The second group can include a halogen, an ester group, an amide group, a carbamate group, an alkoxyl group, a hydroxyl group, a thiol group, a sulfide group, an amine analog, an alkyl, a functionalized alkyl, an alkynyl, an alkenyl, an aryl, or a heteroaryl. Viral infections can also be treated with the trimeric quinones of this invention.

Other objects and advantages will be apparent to those skilled in the art from the following detailed description taken in conjunction with the appended claims.

DESCRIPTION OF PREFERRED EMBODIMENTS

The present invention relates to the development of a method for the regiospecific synthesis of dimeric and trimeric quinone derivatives, also referred to below as biquinones and triquinones respectively. The disclosed method provides control over the placement of functional groups on the carbon atoms of biquinones and trimeric quinones. The invention also relates to new biquinone and trimeric quinone derivatives. The methods and derivatives of this invention facilitate structure-activity-relationship studies that will be crucial to the possible development of new anti-HIV quinone compounds and medicinal compositions.

In one embodiment of this invention, a method for synthesis of a multi-quinone compound includes reacting a hydroxyquinone anion with a first quinone. "Multi-quinone" refers to a chemical compound having more than one quinone monomer. "Quinone" refers to dicarbonyl compounds including two carbonyl groups within a six carbon ring. "Quinone" includes various quinone derivatives including benzoquinone derivatives and naphthoquinone derivatives. The multi-quinone compounds of this invention can include identical quinone monomers or two or more different quinone monomers, such as a biquinone having a benzoquinone monomer bonded to a naphthoquinone monomer.

The first quinone includes at least two directing groups; a first directing group at a carbon-2 (C-2) position of the first quinone and a second directing group at a carbon-3 (C-3). "Carbon-2" or "C-2" refers to one of the six carbon atoms of the quinone core located next to one of the carbons bearing a double bonded oxygen atom (the carbonyl group). "Carbon-3" or "C-3" refers to another of the six carbon atoms of the quinone core next to the C-2 and next to the other carbon bearing a double bonded oxygen atom (the carbonyl group). In one embodiment of this invention, the first directing group is selected from a group consisting of a halogen, including fluorine, chlorine, bromine, iodine, and a non-halogen, and the second directing groups is selected from a group consisting of a halogen and a non-halogen. In one embodiment of this invention the first directing group is a halogen or a non-halogen and the second directing group is iodine or a triflate. Alternatively, as will be appreciated by one skilled in the art, the first directing group can be a halogen, and more particularly iodine, or a non-halogen, and the second directing group can be a halogen, including fluorine, chlorine, bromine, iodine, or a non-halogen. Examples of non-halogen directing groups include sulfonate ester groups, including triflates, tosylates, mesylates, brosylates, as well as phosphates, methoxyl groups, and diazonium groups.

The first quinone includes a structure selected from the group consisting of:

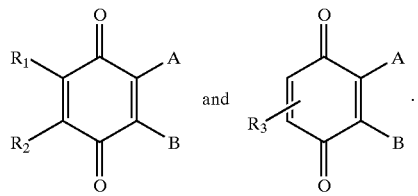

$R_1$–$R_3$ represent various chemical groups. Each of $R_1$ and $R_2$ represent a non-fused group such as hydrogen, an alkoxyl groups, a hydroxyl group, a straight chained or branched-chain saturated alkyl, a straight chained or branched-chain unsaturated alkyl, a straight chained or branched-chain saturated or unsaturated functionalized alkyl, an aryl, a heteroaryl, an ester, and a saturated or unsaturated heterocycle. $R_3$ represents fused ring groups such as a fused aryl, a fused heteroaryl, or a fused polycyclic ring system, and thus the first quinone including $R_3$ represents quinone derivatives such as naphthoquinone and naphthoquinone derivatives. The first directing group is represented by A and is located at the C-2. The second directing group is represented by B and is located at the C-3. The first and second directing groups can be chemically identical, although it is desirable that the first directing group include a different chemical structure than the second directing group. Using a first directing group that is different from a second directing group allows for efficient regiospecific bonding of the hydroxyquinone anion to the first quinone.

The hydroxyquinone anion includes a general structure selected from the group consisting of:

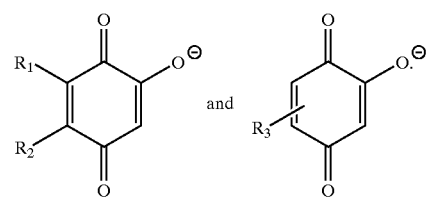

$R_1$–$R_3$ again represent various chemical groups. Each of $R_1$ and $R_2$ represents non-fused groups such as hydrogen, an alkoxyl group, a hydroxyl group, a straight chained or branched-chain saturated alkyl, a straight chained or branched-chain unsaturated alkyl, a straight chained or branched-chain saturated or unsaturated functionalized alkyl, an aryl, a heteroaryl, an ester, and a saturated or unsaturated heterocycle. $R_3$ represents fused ring groups such as a fused aryl, a fused heteroaryl, and a fused polycyclic ring system.

The hydroxyquinone anion can be obtained by reacting a hydroxyquinone in the presence of a base, such as potassium hydroxide (KOH) or cesium carbonate ($Cs_2CO_3$). The hydroxyquinone anion can be isolated from the basic solution by methods known in the art, such as precipitation, or can be left in the solution for further reactions, such as described below. Desirably, the hydroxyquinone includes a hydroxyl group at either the C-2 position or the C-3 position of a hydroxyquinone core, and not both. In one embodiment of this invention, the hydroxyquinone is a dihydroxybenzoquinone derivative.

Reacting the hydroxyquinone anion with the first quinone results in a bond formation between a carbon of the hydroxyquinone anion group and either the carbon (C-2) of the first quinone bearing the first directing group or the carbon (C-3) bearing the second directing group. The reaction is a substitution reaction which proceeds by addition of the hydroxyquinone anion to either the carbon bearing the first directing group or the carbon bearing the second directing group, followed by elimination of the respective directing group. The general reaction of the hydroxyquinone anion and the first quinone is represented by the following reaction, Reaction 1, where X represents either the first or second directing group:

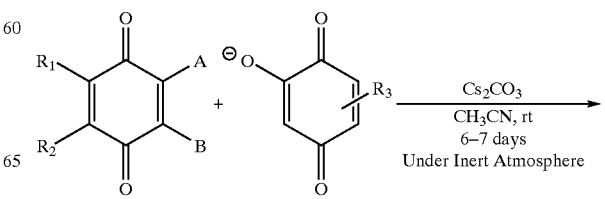

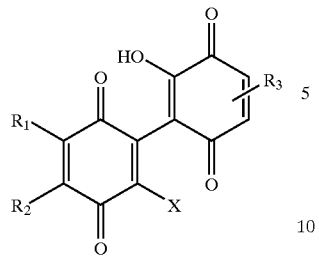

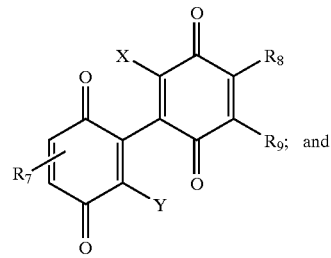

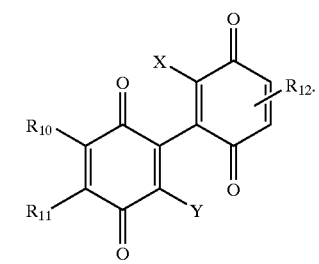

Reaction 1 can occur using any hydroxyquinone anion and any first quinone described above. As shown above, Reaction 1 can occur in a solution containing cesium carbonate and acetonitrile in an inert atmosphere at room temperature (approximately 23° C.) in about six to seven days.

As will be appreciated by one skilled in the art reading this specification, the chemical nature of the first directing group and the second directing groups, and/or the nature and position of $R_1$ and $R_2$ or substituents on $R_3$ of the first quinone (particularly if the first and second directing groups are identical), can control whether bond formation between the hydroxyquinone anion and the first quinone occurs at the carbon bearing the first directing group or the carbon bearing the second directing group.

The reaction of the hydroxyquinone anion and the first quinone results in a biquinone having one of the first and second directing groups at the C-3 of a first quinone monomer and a hydroxyl group at a C-3' of a second quinone monomer. One representative biquinone is shown to the right of the reaction arrow in Reaction 1. The first quinone monomer is obtained from the first quinone and the second quinone monomer is obtained from the hydroxyquinone anion. The C-3 position of the first quinone monomer refers to the same carbon and position as C-3 of the first quinone. The C-3' position of the second quinone monomer refers to a carbon on the second quinone monomer next to the carbon bearing the bond between the first quinone monomer and the second quinone monomer and not bearing a carbonyl group.

The biquinone having one of the first and second directing groups at the C-3 of a first quinone monomer and a hydroxyl group at a C-3' of a second quinone monomer can be further reacted to substitute the hydroxyl group for another chemical group. In one embodiment of this invention, the biquinone can be reacted in the presence of a base and/or a chemical reagent to substitute the hydroxyl group for any chemical group, such as an alkyl ether, a halogen, an amine, a sulfonate ester, and aryl ester, an alkyl ester, or a diazonium group. The resulting biquinones having a general structure shown below, designated as Group 1, are examples of multi-quinone compounds that can be made according to the method of this invention:

Each of $R_1$–$R_4$ and $R_8$–$R_{11}$ represents any non-fused chemical group, such as hydrogen, an alkoxyl group, a hydroxyl group, a straight chained or branched-chain saturated alkyl, a straight chained or branched-chain unsaturated alkyl, a straight chained or branched-chain saturated or unsaturated functionalized alkyl, an aryl, a heteroaryl, an ester, or a saturated or unsaturated heterocycle. Each of $R_5$–$R_7$ and $R_{12}$ represents any fused chemical ring group, such as a fused aryl, a fused heteroaryl, or a fused polycyclic ring system. The quinone monomers having a fused ring can be naphthoquinone monomers, and Group 1 biquinones include dimeric naphthoquinones. Y can include any chemical group, such as an alkyl ether, a halogen, an amine, a sulfonate ester, and aryl ester, or an alkyl ester. X represents the remaining first or second directing group. The first or second directing group can also be substituted with another chemical group.

In one embodiment of this invention, the biquinone compound, having any of the structures shown above for Group 1, can be further reacted with a nucleophile. The nucleophile, through addition and subsequent elimination, substitutes for X, the other of the remaining first and second directing group. In one embodiment of this invention the nucleophile includes carbanions and nucleophiles derived from heteroatoms such as nitrogen, oxygen, sulfur, and phosphorous. Examples of nucleophiles include an amine analog, such as ammonia, alkylamines, and arylamines. The general reaction of the biquinone and an amine analog is represented by the following reaction, Reaction 2, where X is either the first or second directing group:

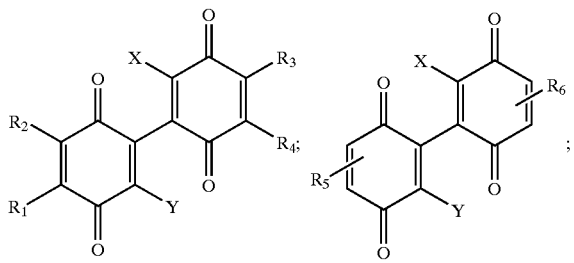

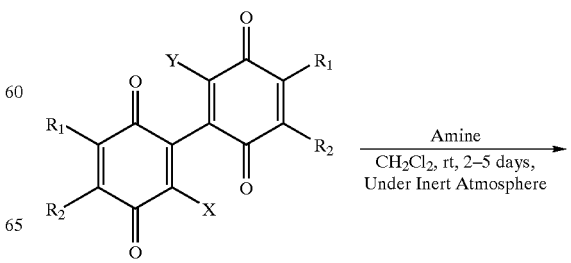

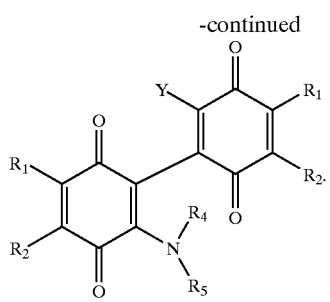

The reaction illustrated by Reaction 2 can occur with any of the biquinones of Group 1 and numerous amine analogs. The chemical groups are described as $R_1$–$R_2$ for demonstrative purposes, and as will be appreciated by one skilled in the art, $R_1$ and $R_2$ of the biquinone can include any of the chemical groups described herein. As will be appreciated by one skilled in the art, the reaction illustrated by Reaction 2 can occur under various conditions depending on the specific biquinone, particularly the nature of the first or second directing group, and the specific amine analog used. Reaction 2 can occur in the presence of methylene chloride ($CH_2Cl_2$) in an inert atmosphere at room temperature (approximately 23° C.) in about 2–5 days.

In an additional embodiment of this invention, the nucleophile is a second hydroxyquinone anion. Reacting the nucleophilic second hydroxyquinone anion with a biquinone of Group 1 results in a new multi-quinone compound. The resulting multi-quinone compound is a trimeric quinone. The reaction may require an additive, such as a crown ether, to enable the polar second hydroxyquinone anion to react with the biquinone by making the second hydroxyquinone anion more soluble in the polar aprotic solvent containing the biquinone. The reaction of a second hydroxyquinone anion and a biquinone selected from Group 1 is represented by the following reaction, Reaction 3, where X is either the first or second directing group:

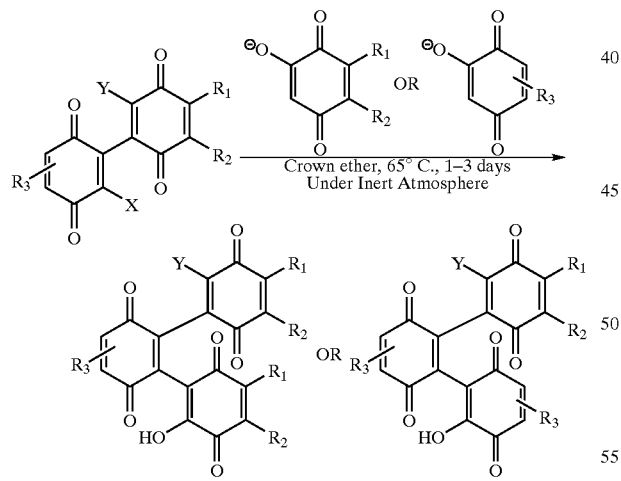

Reaction 3 can occur at a temperature of about 60° C. to 70° C. in a polar aprotic solvent in an inert atmosphere in about 1–3 days. The polar aprotic solution can be obtained through an additive such as crown ether. The chemical groups $R_1$–$R_3$ in Reaction 3 are shown as $R_1$–$R_3$ for demonstrative purposes, and as will be appreciated by one skilled in the art, $R_1$–$R_3$ of the biquinone and second hydroxyquinone can include any of the chemical groups described herein.

The first and second directing groups allow regiospecific control of the quinone-quinone bond formation involving adding hydroxyquinones to the first quinone. Therefore, a first hydroxyquinone anion can be substituted for the first directing group at the C-2 position and a second hydroxyquinone anion can be substituted for the second directing group at the C-3 of the first quinone. Alternatively, a first hydroxyquinone anion can be substituted for the second directing group at the C-3 position and a second hydroxyquinone anion can be substituted for the first directing group at the C-2 of the first quinone. As will be appreciated by one skilled in the art, regiospecific control of the placement of the first hydroxyquinone anion at one of the first or second directing groups usually, at least in part, depends on the chemical nature of the first directing group and the second directing group. For instance, if the first directing group is a triflate group and the second directing group is an iodine atom, the hydroxyquinone anion will selectively substitute for the first directing group, as a triflate is a better directing group and leaving group. Alternatively, if the first directing group is an iodine atom and the second directing group is a triflate group, the hydroxyquinone anion will selectively substitute for the second directing group.

The regiospecific synthetic process provides control over the substitution patterns of biquinones by regiocontrolled substitution of the directing groups in the first quinone by various hydroxyquinone anion derivatives and allows for controlled, high yielding production of numerous biquinone derivatives. Substituting the second quinone anion for either of the first or second directing group remaining on the biquinones of Group 1 results in a trimeric quinone including first, second, and third quinone monomers. The third quinone monomer is obtained from the second hydroxyquinone anion. The trimeric quinone has a hydroxyl group on a C-3" of a third quinone monomer. The C-3" position of the third quinone monomer refers to a carbon on the third quinone monomer next to the carbon bearing the bond between the first quinone monomer and the third quinone monomer and not bearing a carbonyl group. As with the biquinones described above, the hydroxyl group at the C-3" position can be substituted with any chemical group.

The method thus provides a controlled path to obtain various specifically desired trimeric quinone derivatives. Trimeric quinones, designated as Group 2, made by the method of this invention include the general structures:

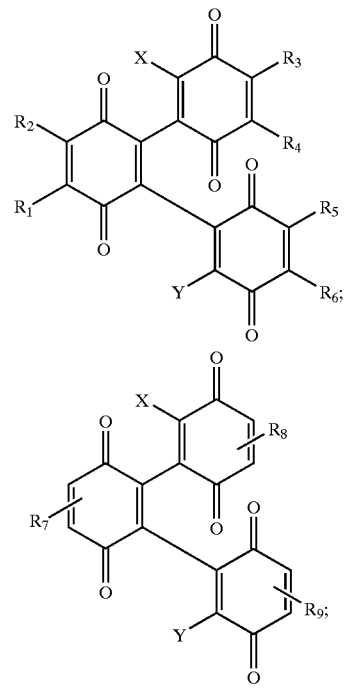

-continued

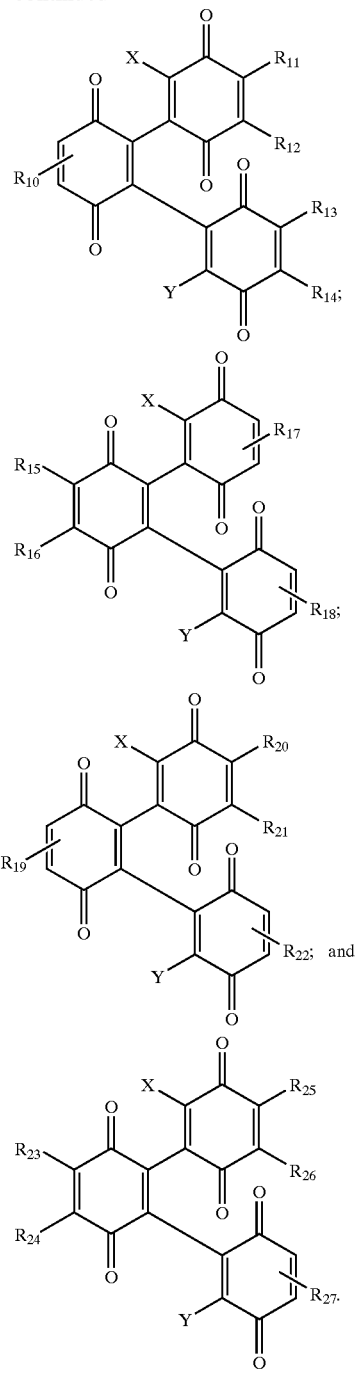

Each of $R_1$–$R_6$, $R_{11}$–$R_{16}$, $R_{20}$, $R_{21}$, and $R_{23}$$R_{26}$ represents a non-fused chemical group from a group including hydrogen, an alkoxyl group, a hydroxyl group, a straight chained or branched-chain saturated, unsaturated, or functionalized alkyl, an aryl, a heteroaryl, an ester, or a saturated or unsaturated heterocycle. Each of $R_7$–$R_{10}$, $R_{17}$–$R_{19}$, $R_{22}$, and $R_{27}$ represents a fused chemical group from a group including a fused aryl, a fused heteroaryl, or a fused polycyclic ring system. X is used in the structures of the Group 2 trimeric quinones to represent chemical groups selected from a group consisting of a halogen, a sulfonate ester group, an alkoxyl group, a diazonium group, an amine analog, an alkynyl, an alkenyl, an aryl, and a heteroaryl. Y is selected from a group consisting of a halogen, a sulfonate ester group, an alkoxyl group, a hydroxyl, a diazonium group, an amine analog, an alkynyl, an alkenyl, an aryl, and a heteroaryl. The trimeric quinones can be further reacted to substitute different chemical groups for X and Y, including additional hydroxyquinone anions to create multi-quinone compounds having more than three quinone monomers.

In an additional embodiment of this invention, a hydroxyquinone anion is chemically substituted through a reaction for a first directing group of the first quinone to form a biquinone compound. The biquinone compound can have any of the general structures shown above for Group 1, and can be further reacted to substitute a non-quinone compound at the second directing group. The biquinone can be reacted with an aryl group or a heteroaryl group in the presence of a catalyst. One method of substituting the second directing group such as a halogen or triflate second directing group, with an aryl group or a heteroaryl group is through a transition-metal catalyzed cross-coupling. The biquinone is reacted with a metalated aryl or metalated heteroaryl ring, such as aryl boronic acid, heteroaryl boronic acid, aryl trialkylstanane, heteroaryl trialkylstanane, aryl zinc halide, or heteroaryl zinc halide, represented in Reaction 4 as "ArM," in the presence of a transition metal possessing coordinated ligands, represented in Reaction 4 as "Pd Ln," such as palladium tetrakistriphenyl phosphine (Pd(PPh$_3$)$_4$) and a cocatalyst such as a base or copper salt. The general reaction, Reaction 4, is represented by the reaction formula below where X is either the first or second directing group:

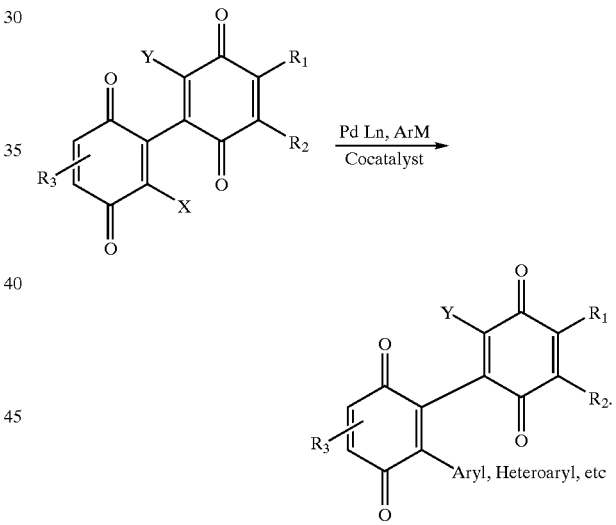

The transition-metal catalyzed cross-coupling can be used to obtain arylated biquinones such as a 3-aryl-2,2'-biquinone, 3-heteroaryl-2,2'-biquinone, 3,3'-diaryl-2,2'-biquinone, or a 3,3'-diheteroaryl-2,2'-biquinone.

As discussed above, it is known in the art that the specific trimeric naphthoquinones isolated from plants in the genus Conospermum have been shown to demonstrate antiviral activity. The method of this invention, particularly when compared to the limited number of isolated trimeric naphthoquinones and the known, low-yielding acid-coupling or base-coupling methods known in the art, allows the full potential of the trimeric quinone structures to be evaluated. The regiospecific synthesis methods of this invention allow one skilled in the art to create various specifically desired trimeric quinone derivatives, including, for example, the trimeric naphthoquinones obtained from the plants in the genus Conospermum and other trimeric naphthoquinone derivatives. The various trimeric quinone derivatives of this invention demonstrate antiviral activity and can be used in anti-HIV compositions to fight AIDS.

In addition, it has been discovered that biquinone derivatives of this invention demonstrate antiviral activity. Thus this invention provides for an antiviral composition including a biquinone, and particularly a biquinone described above having a structure designated as Group 1. The invention also provides for an antiviral composition including a trimeric quinone, and particularly a trimeric quinone described above having a structure designated as Group 2.

One aspect of this invention relates to a method for treating a viral infection. The viral infection is treated by administering to a host an antiviral biquinone compound including a first group at a carbon-3 (C-3) position and a second group at a carbon-3' (C-3') position. The first group is a chemical group other than hydrogen and includes one of, for example, a halogen, an alkoxyl group, a hydroxyl, a thiol, an ester, a carbamate, a primary, secondary, or tertiary aliphatic amine, a cyclic amine, an alkyl, a functionalized alkyl, an alkyne, an alkene, an aryl, and a heteroaryl. The second group is also a chemical group other than hydrogen and includes one of, for example, a halogen, an alkoxyl group, a hydroxyl, a thiol, an ester, a carbamate, a primary, secondary, or tertiary aliphatic amine, a cyclic amine, an alkyne, an alkyl, a functionalized alkyl, an alkene, an aryl, and a heteroaryl.

The activity of the antiviral multi-quinone compounds of this invention can be demonstrated through in vitro antiviral assays known in the art. The assays desirably measure the concentration of the multi-quinone that allows for 50% survival of CEM-T4 cells infected with HIV-1 and the concentration of multi-quinone that kills 50% of uninfected CEM-T4 cells. One skilled in the art will appreciate that other known assays or tests for determining antiviral activity may be used.

Multi-quinone compounds of the present invention have been shown to inhibit retroviruses, particularly the human immunodeficiency virus, including different strains of HIV-1. As one skilled in the art will appreciate, the compounds of the present invention will likely inhibit other retroviruses, particularly viruses of the Lentivirus genus, and possibly other types of viruses. Examples of viruses that may be treated in accordance with the present invention include, without limitation, human immunodeficiency virus type 2 (HIV-2), human T-cell lymphotropic virus type 1 (HTLV-1) and type 2 (HTLV-2), simian immunodeficiency virus (SIV), avian sarcoma virus (ASV), feline leukemia virus (FLV), feline immunodeficiency virus (FIV), bovine immunodeficiency virus (BIV), bovine leukemia virus (BLV), murine leukemia virus (MLV), maedi-visna virus (MVV), equine infectious anemia virus (EIAV), caprine arthritis encephalitis virus (CAEV), strains of the herpes simplex virus (HSV), and hepatitis viruses (HV) such as HAV, HBV, HCV, HDV, HEV.

The multi-quinone compounds may be formulated into various compositions for use in therapeutic antiviral treatment compositions. Antiviral compositions of this invention include one or more antiviral multi-quinone compound of this invention, as well as a pharmaceutically acceptable carrier. Pharmaceutically acceptable carriers and methods of administration are well-known to those skilled in the art. The choice of pharmaceutical acceptable carrier will be determined in part by the particular multi-quinone compound, as well as by the particular method used to administer the composition.

The multi-quinone compounds of this invention can be used to treat virally-infected people or animals, and can include various compositions or formulations for treatment. One skilled in the art will appreciate the numerous possible formulations that can be used to administer the multi-quinone compounds of this invention. Liquid solutions, such as water, saline, gel-capsules containing a predetermined amount of the active ingredient are examples of suitable formulations for use with the multi-quinone compounds of this invention. Tablets including one or more of lactose, mannitol, corn starch, gelatin, colorants, diluents, buffering agents, moistening agents, preservatives, flavoring agents, and pharmacologically compatible carriers are other examples of suitable formulations for use with the multi-quinone compounds of this invention. Other formulations include, without limitation, lozenges, aerosols, creams, emulsions, gels, and rectal or vaginal suppositories.

The particular multi-quinone compound will play an important role in determining the dose provided to the host. The dosage is desirably sufficient to invoke an antiviral response in the infected host in a reasonable timeframe. Side-effects may also play a part in determining dosage.

The multi-quinone compounds of this invention can also be used in combination with other known anti-viral, particularly anti-HIV, compounds or treatment agents for AIDS. Examples of other compounds and treatments include protease inhibitors, nucleoside reverse transcriptase inhibitors (e.g. AZT), non-nucleoside reverse transcriptase inhibitors, integrase inhibitors, cell fusion inhibitors, immunomodulators, immunostimulents, and antibiotics. The multiquinone compounds of this invention can be included in combination or treatment regiments of AIDS drugs known in the art.

EXAMPLES

To demonstrate the method of this invention and the antiviral activity of the multi-quinone compounds of this invention, two biquinones and one trimeric quinone were prepared.

Sample 1

The biquinone 8-(3-Chloro-1,4-dioxo-1,4-dihydronapthalen-2-yl)-9-hydroxy-3-methyl-3-(4-methyl-pent-3-enyl)-3H-benzo[f]chromene-7,10-dione, referred to below as chlorohydroxybiquinone, having the general structure:

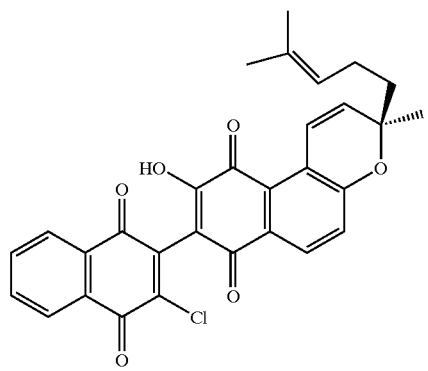

was prepared from a reaction of 2,3-dichloro-1,4-naphthoquinone with teretifolione B. 0.302 grams (1.33 millimoles) of 2,3-dichloro-1,4-naphthoquinone, 0.430 grams (1.33 millimoles) of teretifolione B, and 2 millimoles of cesium carbonate were placed in a 25 milliliter round bottom flask fitted with a T-bore stopcock. After 3 vacuum and argon cycles to obtain an inert atmosphere, 10 milliliters of anhydrous acetonitrile ($CH_3CN$) was added to the flask and the suspension was stirred at room temperature (approximately 23° C.) for seven days. The mixture was acidified with concentrated hydrochloric acid (HCl) to obtain a pH of 2 by litmus testing. The suspension was poured into a 100 milliliters of water and stirred for one hour to dissolve any remaining traces of cesium carbonate. The precipitated biquinone was filtered and air-dried for 3 days at room temperature. The procedure yielded 0.650 grams (95% yield) of the chlorohydroxybiquinone which had a brilliant red color. The structure of the chlorohydroxybiquinone was confirmed by NMR analysis.

The chlorohydroxybiquinone was tested for anti-HIV activity by the CEM-T4 cytoprotection assay which measures the inhibition of viral cytopathogenic effects. CEM-T4 cells used for the assay were maintained in RPMI-1640 culture medium containing 2 millimoles L-glutamine and 25 millimoles HEPES, and supplemented with 10% fetal bovine serum, 50 units/milliliter of penicillin G, and 50 microgram/milliliter streptomycin sulfate. The antiviral assays were performed in 96-well tissue culture plates. Cells were treated with polybrene at a concentration of 2 microgram/milliliter, and $1 \times 10^4$ cells were dispensed into each well. Appropriate concentrations of the biquinone were prepared in sterile DMSO and diluted with culture medium to the desired concentrations. Each dilution of test compound was added to multiple wells of cells, and the cells were incubated at 37° C. for one hour. Cells were then infected at a multiplicity of infection of 0.025 $TCID_{50}$/cell by the addition of a diluted stock of the HTLV-IIIB strain of HIV-1. Compounds were tested in triplicate wells per concentration for infected cells and in duplicate wells per concentration for uninfected cells.

Assay plates were incubated at 37° C. in a humidified 5% carbon dioxide ($CO_2$) atmosphere and examined microscopically for toxicity and/or cytopathogenic effect. Once the viral cytopathogenic effect was maximal (the eighth day post-infection), the surviving cells in each test well were quantified using the MTT assay known in the art and described in Pauwels et al., "Rapid and Automated Tetrazolium-based Colorimetric Assay for the Detection of Anti-HIV Compounds," J. Virol. Meth., 1988, Vol. 20, 309–321, herein incorporated by reference. Cytoprotection and toxicity are reported as the concentration of drug required to inhibit viral-mediated cytopathicity by 50% of infected controls ($ID_{50}$) and to cause reduction of cell growth by 50% of uninfected controls ($TD_{50}$), respectively. When a dose-dependent effect for either anti-HIV activity or cytotoxicity was observed, values for the 50% effective dose were calculated using the dose-effect analysis software of Chou and Chou, available from Elsevier-Biosoft.

The $ID_{50}$ of the biquinone was determined to be 0.43 micromolar and the $TD_{50}$ was determined to be 2.7 micromolar.

Sample 2

The chlorohydroxybiquinone of Sample 1 was further reacted to obtain 8-(3-Chloro-1,4-dioxo-1,4-dihydro-napthalen-2-yl)-9-methoxy-3-methyl-3-(4-methyl-pent-3-enyl)-3H-benzo[f]chromene-7,10-dione, referred to below as chloromethoxybiquinone, having the general structure:

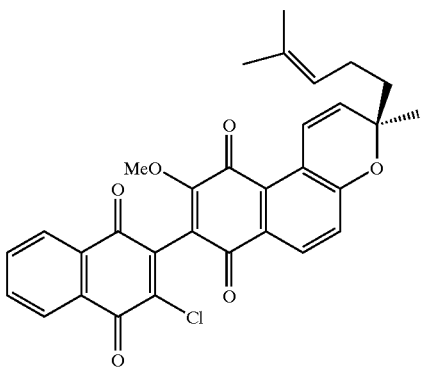

0.250 grams (0.49 millimoles) of the chlorohydroxybiquinone of Sample 1 and 0.145 grams (0.98 millimoles) trimethyloxonium tetrafluoroborate were placed into a 100 milliliter round bottom flask fitted with a T-bore stopcock. After 3 vacuum and argon cycles to obtain an inert atmosphere, 60 milliliters of anhydrous methylene chloride ($CH_2Cl_2$) was added and the suspension stirred at room temperature for 30 minutes. 0.096 grams (0.98 millimoles) of N,N-diisopropylethylamine was added and the solution was stirred for an additional 3 hours. The solution was diluted with 60 milliliters of methylene chloride and the mixture was washed successively with 150 milliliters of water containing 3 drops (2 milliliters) of concentrated hydrochloric acid and 150 milliliters of 10% by weight aqueous $NaHCO_3$. The organic layer was dried with $MgSO_4$, filtered, and evaporated to yield 0.166 grams (64% yield) of the chloromethoxybiquinone. The chloromethoxybiquinone had a bronze color and the structure was confirmed by NMR analysis.

The chloromethoxybiquinone was tested for antiviral activity by CEM-T4 cytoprotection assay as described above for Sample 1. The $ID_{50}$ was determined to be 2.3 micromolar and the $TD_{50}$ was determined to be 5.4 micromolar.

Sample 3

The trimeric quinone 3-Hydroxy-3'-(9-methoxy-3,3-dimethyl-7,10-dioxo-7,10-dihydro-3H-benzo[f]chromen-8-yl)-2,2'-binaphthalenyl-1,4,1',4'-tetraone, referred to below as the trimeric quinone, having the general structure:

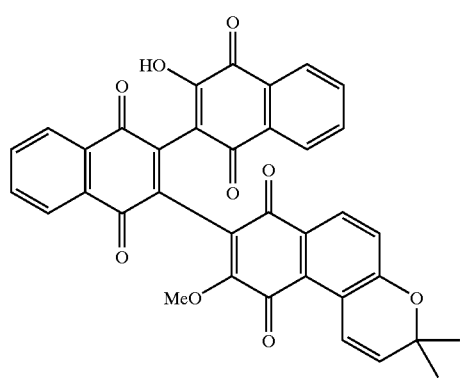

was prepared from reaction of 0.220 grams (0.48 millimoles) of 8-(3-Chloro-1,4-dioxo-1,4-dihydronaphthalen-2-yl)-9-methoxy-3,3-dimethyl-3H-benzo[f] chromene-7,10-dione, 0.102 grams (0.48 millimoles) of the potassium salt of 2-hydroxy-1,4-naphthoquinone, and 0.127 grams (0.48 millimoles) of 18-crown-6 (0.127 grams, 0.48 millimoles) in a 25 milliliter round bottom flask fitted with a T-bore stopcock. After 3 vacuum and argon cycles to obtain an inert atmosphere, 15 milliliters of anhydrous N-methyl pyrrolidinone (NMP) was added. The suspension was stirred at 65° C. for 2 days. The resulting dark red suspension was cooled to room temperature and then acidified with concentrated hydrochloric acid to a pH of 2 using a litmus test. The organic layer was dried using $MgSO_4$, filtered, and the crude product was crystallized from methanol to give 0.04 grams (14% yield) of the trimeric quinone. The trimeric quinone had an orange color and the structure was confirmed by NMR analysis.

The trimeric quinone was tested for antiviral activity by CEM-T4 cytoprotection assay as described above for Sample 1. The $ID_{50}$ was determined to be 8.8 micromolar and the $TD_{50}$ was determined to be 17 micromolar.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method for synthesis of a multi-quinone compound, comprising:

reacting a hydroxyquinone anion with a first quinone possessing a first directing group at a C-2 of the first quinone and a second directing group at a C-3 of the first quinone; and obtaining a biquinone having one of the first and second directing groups at a C-3 of a first quinone monomer and a hydroxyl group at a C-3' of a second quinone monomer;

wherein one of the first and second directing groups is selected from a group consisting of a fluorine, chlorine, bromine, iodine, and a non-halogen, and another of the first and second directing groups is selected from a group consisting of iodine and a non-halogen.

2. The method of claim 1, further comprising obtaining the hydroxyquinone anion by reacting a hydroxyquinone in a presence of a base.

3. The method of claim 2, wherein the hydroxyquinone includes a hydroxyl group at one of a C-2 position and a C-3 position of a hydroxyquinone core.

4. The method of claim 3, wherein the hydroxyquinone is a dihydroxybenzoquinone derivative.

5. The method of claim 1, wherein the non-halogen first and second directing groups are selected from a group consisting of a sulfonate ester group, a triflate, a tosylate, a mesylate, a brosylate, a methoxy group, and a diazonium group.

6. The method of claim 1, wherein the reaction of the hydroxyquinone anion and the first quinone occurs in an inert atmosphere.

7. The method of claim 6, wherein the biquinone is:

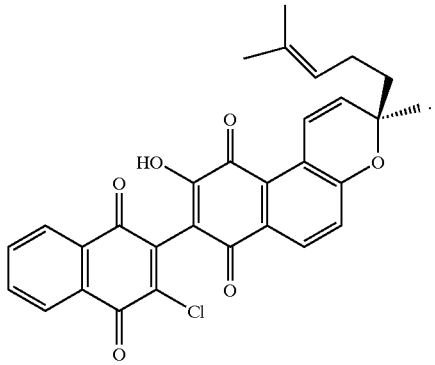

8. The method of claim 1, further comprising reacting the biquinone in the presence of a base to substitute the hydroxyl group with a chemical group selected from the group consisting of an alkyl ether, a halogen, an amine, a sulfonate esters, an aryl, an aryl esters, an alkyl ester, an alkyl amide, an aryl amide, and a carbamate.

9. The method of claim 8, wherein the multi-quinone compound has a structure selected from a group consisting of:

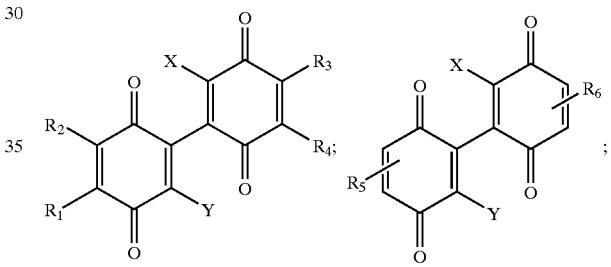

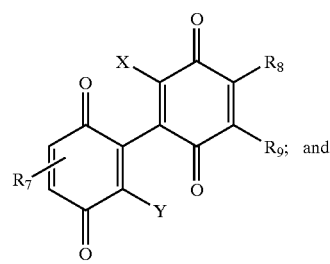
and

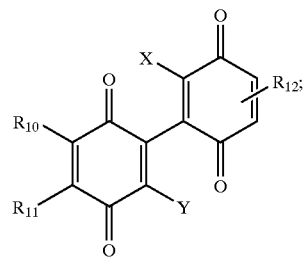

wherein each of $R_1$–$R_{12}$ is selected from a group consisting of hydrogen, an alkoxyl group, a hydroxyl group, an ester, a straight chained or branched-chain saturated alkyl, a straight chained or branched-chain unsaturated alkyl, a straight chained or branched-chain saturated or unsaturated functionalized alkyl, an aryl, a fused aryl, a fused O-heterocycle, and a fused polycyclic ring system; Y is the chemical group selected from the group consisting of an alkyl ester, a halogen, an amine, a sulfonate ester, an aryl ester, and an alkyl ethers; and X is one of the first and second directing groups.

10. The method of claim 9, wherein the biquinone is:

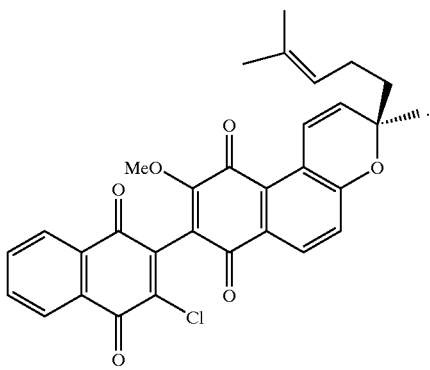

11. The method of claim 8, further comprising substituting the hydroxyquinone anion for one of the first and second directing groups and reacting the biquinone with a nucleophile, the nucleophile substituting for the other of the first and second directing group.

12. The method of claim 11, wherein the nucleophile is a second hydroxyquinone anion and the multi-quinone compound is a trimeric quinone.

13. The method of claim 12, wherein the multi-quinone compound is selected from a group consisting of:

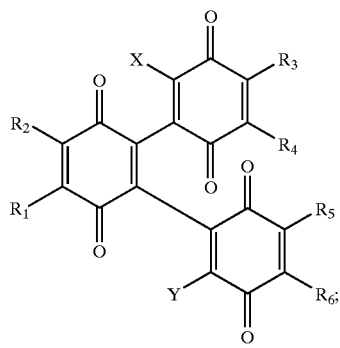

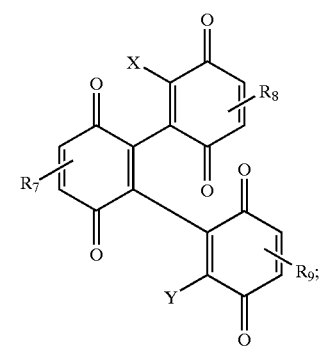

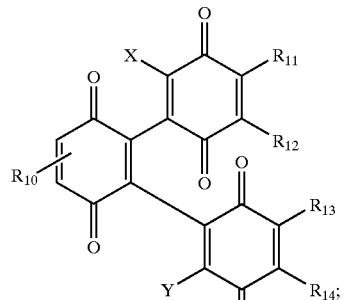

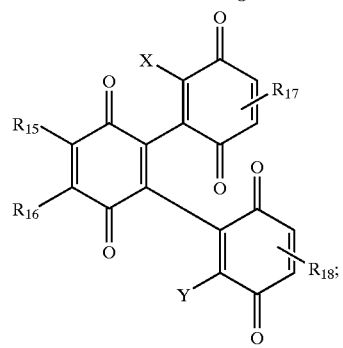

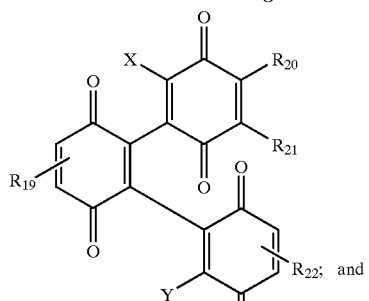

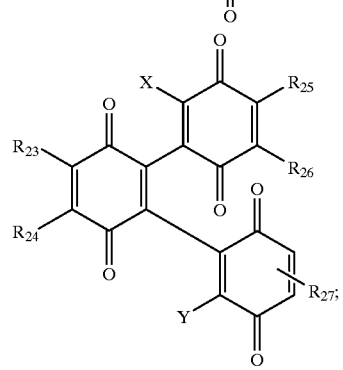

wherein each of $R_1$–$R_{27}$ is selected from a group consisting of hydrogen, an alkoxyl group, a hydroxyl group, a straight chained or branched-chain saturated or unsaturated alkyl, a straight chained or branched-chain saturated or unsaturated functionalized alkyl, an aryl, a fused aryl, a fused O-heterocycle, and a fused polycyclic ring system; X is selected from a group consisting of a sulfonate ester group, an alkoxyl group, an amine analog, an alkynyl, an alkenyl, and an aryl; and Y is selected from a group consisting of a halogen, a hydroxyl, an ester group, a sulfonate ester group, an alkoxyl group, an amine analog, an alkynyl, an alkenyl, and an aryl, and a heteroaryl.

14. The method of claim 1, further comprising substituting the other of the first and second directing group of the biquinone compound with one of a saturated aryl and an unsaturated aryl group through transition metal catalyzed cross-coupling.

15. The method of claim 8, further comprising substituting the other of the first and second directing group of the biquinone compound with one of a saturated aryl and an unsaturated aryl group through transition metal catalyzed cross-coupling.

16. The method of claim 8, wherein the nucleophile is selected from the group consisting of a carbanion, an amine, a thiol, an alkoxide, and a phosphorous derivative.

17. A biquinone selected from a group consisting of:

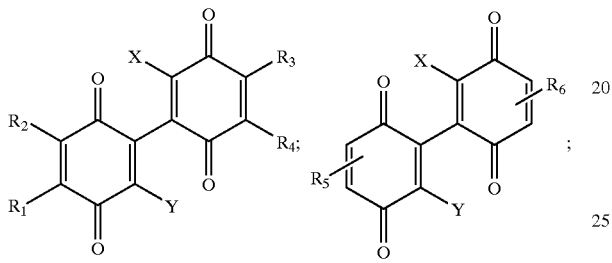

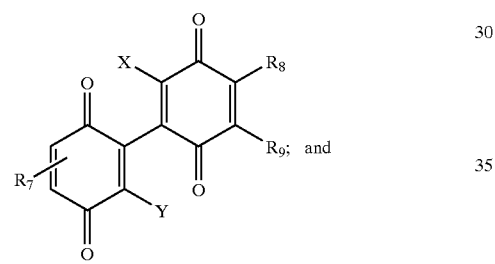

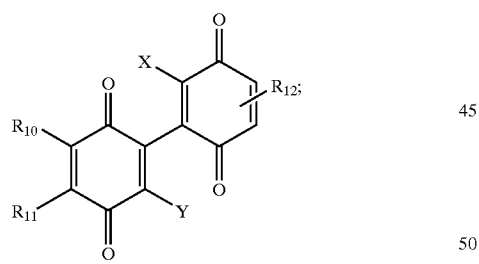

wherein each of $R_1$–$R_{12}$ is selected from a group consisting of hydrogen, an alkoxyl group, a hydroxyl group, a straight chained or branched-chain saturated or unsaturated alkyl, a straight chained or branched-chain saturated or unsaturated functionalized alkyl, an aryl, a fused aryl, a fused O-heterocycle, and a fused polycyclic ring system; X is selected from a group consisting of a halogen, an alkyl ether, a sulfonate ester group, an alkoxyl group, a hydroxyl group, a diazonium group, an amine analog, an alkynyl, an alkenyl, and an aryl; and Y is selected from a group consisting of a halogen, a sulfonate ester group, an alkoxyl group, a diazonium group, an amine analog, an alkynyl, an alkenyl, and an aryl.

18. A pharmaceutical composition comprising the biquinone of claim 17 and a pharmaceutically acceptable carrier.

19. A trimeric quinone selected from a group consisting of:

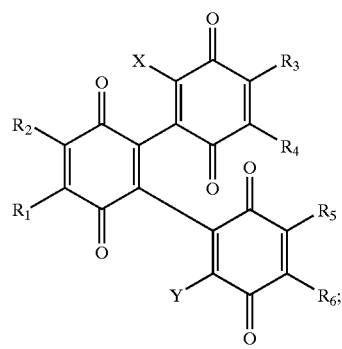

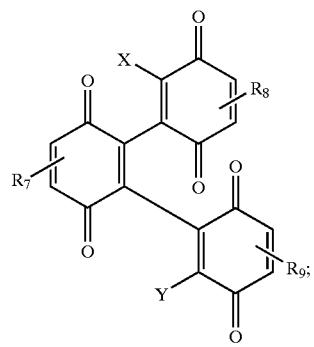

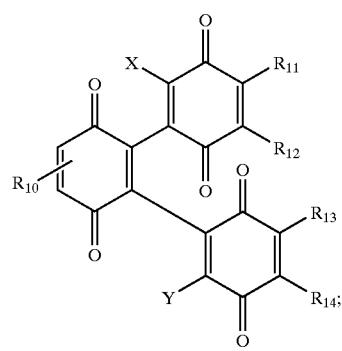

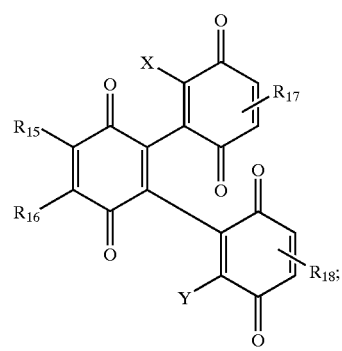

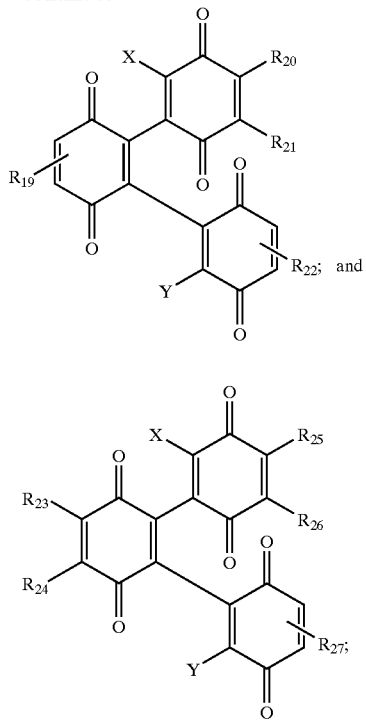

wherein each of $R_1$–$R_{27}$ is selected from a group consisting of hydrogen, an alkoxyl group, a hydroxyl group, a straight chained or branched-chain saturated or unsaturated alkyl, a straight chained or branched-chain saturated or unsaturated functionalized alkyl, an aryl, a fused O-heterocycle, and a fused polycyclic ring system; X is selected from a group consisting of a halogen, an ester group, a sulfonate ester group, an alkoxyl group, a hydroxyl, an amine analog, an alkynyl, an alkenyl and an aryl; and Y is selected from a group consisting of a halogen, an ester group, a sulfonate ester group, an alkoxyl group, an amine analog, an alkynyl, an alkenyl, and an aryl.

20. The trimeric quinone of claim 19, wherein the trimeric quinone is:

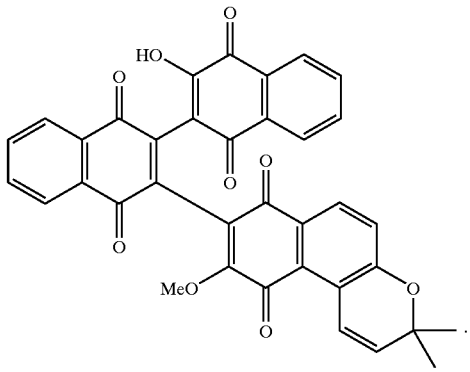

21. A pharmaceutical composition comprising the trimeric quinone of claim 19, and a pharmaceutically acceptable carrier.

* * * * *